(12) United States Patent
Goto et al.

(10) Patent No.: US 9,116,106 B2
(45) Date of Patent: Aug. 25, 2015

(54) X-RAY DETECTION APPARATUS FOR X-RAY FLUORESCENCE ANALYSIS

(71) Applicant: HORIBA, Ltd., Kyoto (JP)

(72) Inventors: Satoru Goto, Kyoto (JP); Yoshito Komada, Kyoto (JP); Yoshiyuki Nakajima, Kyoto (JP)

(73) Assignee: HORIBA, LTD. (JP)

( * ) Notice: Subject to any disclaimer, the term of this patent is extended or adjusted under 35 U.S.C. 154(b) by 202 days.

(21) Appl. No.: 13/861,867

(22) Filed: Apr. 12, 2013

(65) Prior Publication Data

US 2013/0272497 A1 Oct. 17, 2013

(30) Foreign Application Priority Data

Apr. 12, 2012 (JP) .................................. 2012-91311

(51) Int. Cl.
*G01N 23/223* (2006.01)
*G21K 1/02* (2006.01)

(52) U.S. Cl.
CPC ................ *G01N 23/223* (2013.01); *G21K 1/02* (2013.01); *G21K 1/025* (2013.01); *G01N 2223/076* (2013.01); *G01N 2223/316* (2013.01); *G01N 2223/317* (2013.01); *G01N 2223/6113* (2013.01)

(58) Field of Classification Search
CPC .......... G01N 23/223; G01N 2223/076; G01N 2223/317; G01N 2223/316; G21K 1/02; G21K 1/025; G21K 1/04; G21K 1/043
USPC .............................................. 378/44–50, 161
See application file for complete search history.

(56) References Cited

U.S. PATENT DOCUMENTS

| | | | | |
|---|---|---|---|---|
| 3,925,660 A * | 12/1975 | Albert | ............................. | 378/45 |
| 5,408,512 A * | 4/1995 | Kuwabara et al. | .............. | 378/45 |
| 6,028,911 A * | 2/2000 | Kawahara | ........................ | 378/44 |
| 6,038,280 A * | 3/2000 | Rossiger et al. | ................ | 378/50 |
| 6,292,532 B1 * | 9/2001 | Kawahara et al. | .............. | 378/49 |
| 6,337,897 B1 * | 1/2002 | Kawahara et al. | .............. | 378/45 |
| 6,522,718 B2 * | 2/2003 | Sato | ............................... | 378/50 |
| 6,798,863 B2 * | 9/2004 | Sato | ............................... | 378/46 |
| 6,810,106 B2 * | 10/2004 | Sato | ............................... | 378/50 |
| 6,965,663 B2 * | 11/2005 | Ohzawa | .......................... | 378/44 |
| 7,065,174 B2 * | 6/2006 | Sipila et al. | ..................... | 378/44 |
| 7,375,359 B1 * | 5/2008 | Grodzins | ................... | 250/515.1 |
| 7,424,093 B2 * | 9/2008 | Fukai et al. | ..................... | 378/44 |
| 7,428,293 B2 * | 9/2008 | Fukai et al. | ..................... | 378/44 |
| 7,436,926 B2 * | 10/2008 | Matoba et al. | .................. | 378/45 |
| 7,443,959 B2 * | 10/2008 | Kantonen et al. | ............... | 378/44 |
| 7,474,730 B2 * | 1/2009 | Puusaari et al. | ................ | 378/48 |

(Continued)

FOREIGN PATENT DOCUMENTS

JP 2002-214167 A 7/2002

*Primary Examiner* — Allen C. Ho
(74) *Attorney, Agent, or Firm* — Cantor Colburn LLP

(57) ABSTRACT

The X-ray detection apparatus is equipped with an X-ray irradiation unit, an X-ray detector, and a movable collimator having a plurality of apertures. The collimator is provided with a window unit through which light passes, and the apertures and the window unit are aligned in one direction. The collimator moves in the direction so as to change the diameter of an aperture for narrowing X-rays from the X-ray irradiation unit to be used for irradiation of a sample and move to a position to allow an imaging unit to photograph a sample through the window unit. It becomes possible to photograph a sample even in a state where the X-ray irradiation unit, the X-ray detector and the collimator are positioned proximally to each other.

8 Claims, 5 Drawing Sheets

(56) References Cited

U.S. PATENT DOCUMENTS

| | | | |
|---|---|---|---|
| 7,508,907 B2* | 3/2009 | Sasayama | 378/45 |
| 7,515,685 B2* | 4/2009 | Iwamoto et al. | 378/44 |
| 7,587,025 B2* | 9/2009 | Fukai et al. | 378/86 |
| 7,627,088 B2* | 12/2009 | Matoba et al. | 378/140 |
| 7,634,053 B2* | 12/2009 | Matoba | 378/44 |
| 7,680,248 B2* | 3/2010 | Matoba | 378/140 |
| 7,688,942 B2* | 3/2010 | Klein | 378/44 |
| 7,796,726 B1* | 9/2010 | Gendreau et al. | 378/46 |
| 7,916,834 B2* | 3/2011 | Piorek et al. | 378/44 |
| 7,970,101 B2* | 6/2011 | Sakai et al. | 378/46 |
| 8,000,439 B2* | 8/2011 | Matoba | 378/46 |

* cited by examiner

X-RAY DETECTION APPARATUS FOR X-RAY FLUORESCENCE ANALYSIS

CROSS-REFERENCE TO RELATED APPLICATIONS

The present invention claims priority under 35 U.S.C. §119 to Japanese Application No. 2012-91311 filed Apr. 12, 2012, the entire content of which is incorporated herein by reference.

BACKGROUND

1. Technical Field

The present invention relates to an X-ray detection apparatus for irradiating a sample with X-rays and detecting fluorescent X-rays generated from the sample.

2. Description of Related Art

X-ray fluorescence analysis is an analytical method including steps of: irradiating a sample with X-rays; detecting fluorescent X-rays generated from the sample; and making a qualitative analysis or a quantitative analysis of elements contained in the sample according to a fluorescent X-ray spectrum. In general, an X-ray detection apparatus is provided with a collimator for narrowing X-rays to be used for irradiation or fluorescent X-rays, in order to inhibit detection of X-rays other than fluorescent X-rays generated from an analysis object part of a sample. A collimator is prepared by forming an aperture at an object which blocks X-rays, so as to selectively allow fluorescent X-rays from an analysis object part of a sample to enter an X-ray detector by allowing X-rays to be used for irradiation of the analysis object part of the sample or fluorescent X-rays generated from the analysis object part of the sample to pass through the collimator and blocking other X-rays. The size of an analysis object part of a sample varies depending on the type of a sample, the purpose of analysis or the like, and the range to narrow X-rays or fluorescent X-rays also varies. Therefore, an X-ray detection apparatus equipped with a collimator including a plurality of apertures having different diameters has been developed so that the size of an aperture can be changed by moving the collimator. Such an X-ray detection apparatus is disclosed in Japanese Patent Application Laid-Open No. 2002-214167. Moreover, some X-ray detection apparatuses are equipped with an imaging unit for photographing a sample.

SUMMARY OF THE INVENTION

There is a need for downsizing of an X-ray detection apparatus in order to respond to the microminiaturization of a sample such as a circuit board. There is also a demand for downsizing of an X-ray detection apparatus in order to realize easier X-ray fluorescence analysis. In a downsized X-ray detection apparatus, an X-ray irradiation unit, an X-ray detector, a sample support unit and a collimator are located as proximally as practicable to each other. In such an X-ray detection apparatus, interruption by any one of the X-ray irradiation unit, the X-ray detector and the collimator makes it difficult to photograph a sample. Although there is a technique to move a sample support unit so as to enable photographing of a sample, such a technique has a problem that it is impossible to photograph a sample at a position where the sample is irradiated with X-rays.

The present invention has been made in view of such problems, and the object thereof is to provide a downsized X-ray detection apparatus which can photograph a sample.

An X-ray detection apparatus according to the present invention is characterized by comprising: an X-ray irradiation unit; a sample support unit configured to support a sample to be irradiated with X-rays from the X-ray irradiation unit; an X-ray detector configured to detect X-rays generated from the sample; an imaging unit configured to obtain an optical image of the sample supported by the sample support unit; and a collimator which includes a plurality of apertures having different sizes and a window unit that light used for obtaining an optical image of the sample can pass through, wherein the collimator moves to change an aperture that X-rays pass through and moves to shift the window unit to a position that allows the imaging unit to obtain an optical image of the sample through the window unit.

In an X-ray detection apparatus of the present invention which is equipped with an X-ray irradiation unit and an X-ray detector and detects X-rays from a sample, a movable collimator is provided with a window unit and moves to a position which allows an imaging unit to obtain an optical image of a sample through the window unit. It is possible to photograph a sample through the window unit while the collimator is at a predetermined position, although it is impossible to photograph a sample while the collimator is at a position to narrow X-rays.

An X-ray detection apparatus according to the present invention is characterized in that the apertures and the window unit of the collimator are aligned in one direction, and the collimator can move in the direction.

In the present invention, the apertures and the window unit of the collimator are aligned in one direction and the collimator moves in a reciprocating motion in the direction. Both of change of the diameter of an aperture and movement of the window unit to a position to enable photographing are executed by one action.

An X-ray detection apparatus according to the present invention is characterized by further comprising: a shaft parallel to the one direction; and a linear drive motor, which has a drive shaft parallel to the shaft, configured to drive the drive shaft linearly in a longitudinal direction, wherein the shaft is connected with the drive shaft, and the collimator is connected with the shaft.

In the present invention, the collimator is connected with a shaft, which is reciprocated in the longitudinal direction by the linear drive motor, and is moved by the operations of the linear drive motor.

An X-ray detection apparatus according to the present invention is characterized in that an end part of the X-ray irradiation unit from which X-rays exit, an end part of the X-ray detector through which X-rays enter and the collimator are located in a sealed box, and the shaft is piercing through a wall of the sealed box and is provided with a shaft seal configured to maintain the sealing condition.

In the present invention, an end part of the X-ray irradiation unit from which X-rays exit, an end part of the X-ray detector through which X-rays enter and the collimator are located in a sealed box and the shaft is provided with a shaft seal, so that X-ray detection is performed in a sealed state.

An X-ray detection apparatus according to the present invention is characterized in that the sample support unit has a horizontal plate shape and has an X-ray transmissive window on which a sample is to be placed, the imaging unit is located immediately below the sample support unit, the collimator moves along an undersurface of the sample support unit, the X-ray irradiation unit is located at a position to irradiate the X-ray transmissive window with X-rays from obliquely below, and the X-ray detector is located at a position to detect X-rays which have been transmitted by the X-ray transmissive window obliquely downward.

In the X-ray detection apparatus of the present invention, all mechanisms to be used for detection of fluorescent X-rays, such as the X-ray irradiation unit, the X-ray detector and the collimator, are located below the sample support unit, and a sample is placed on the sample support unit. Accordingly, there is no structure that obstructs placement and replacement of a sample.

An X-ray detection apparatus according to the present invention is characterized in that the window unit is constituted of a transparent plate.

In the present invention, the window unit is constituted of a transparent member, so that the window unit can prevent falling of a sample from the X-ray transmissive window.

With the present invention, it is possible to photograph a sample without moving the sample from a position where the sample is irradiated with X-rays, and therefore it is possible to photograph a sample at a position where the sample is irradiated with X-rays. The present invention has beneficial effects such that it becomes possible to photograph a sample even in a state where an X-ray irradiation unit, an X-ray detector and a collimator are positioned proximally to each other and it becomes possible to downsize an X-ray detection apparatus which enables photographing of a sample as well as detection of fluorescent X-rays.

The above and further objects and features of the invention will more fully be apparent from the following detailed description with accompanying drawings.

DETAILED DESCRIPTION

Figure 1:
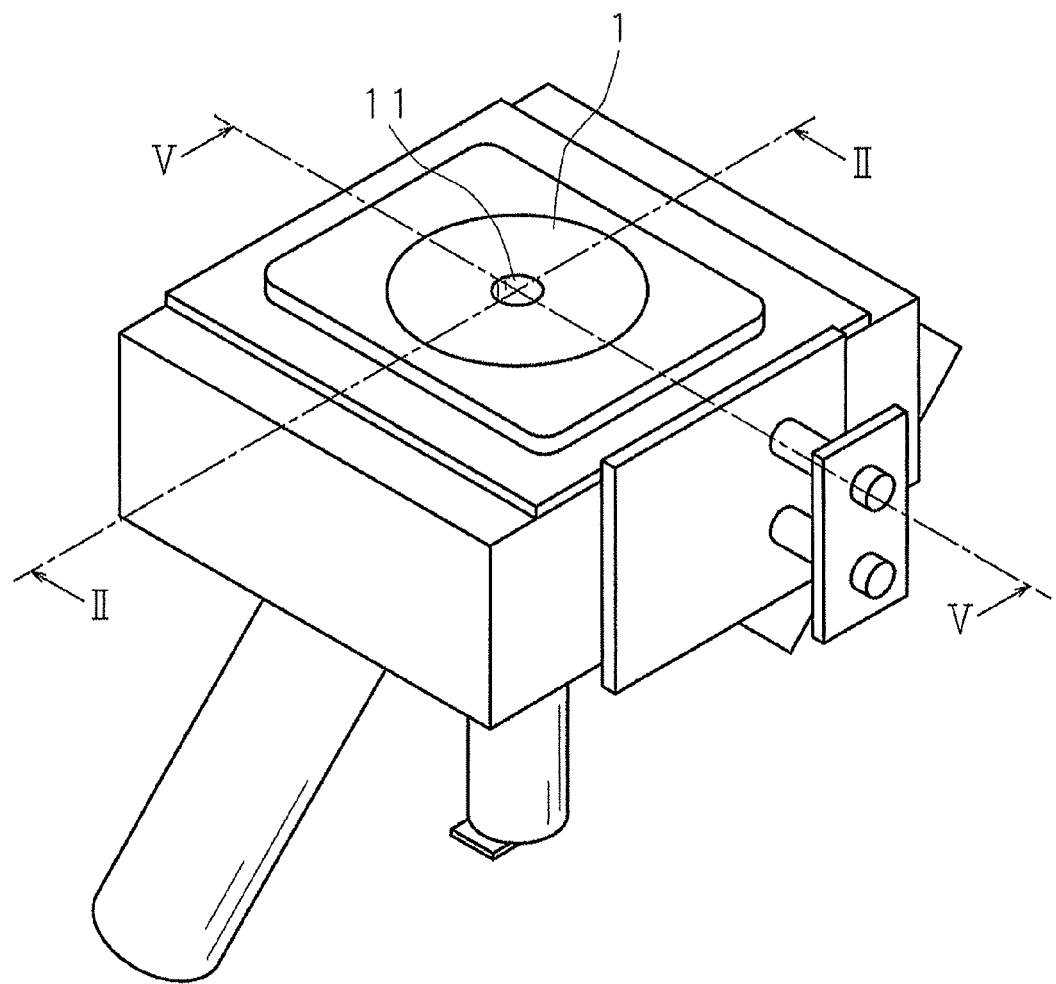
FIG. 1 is a schematic perspective view for illustrating the main structure of an X-ray detection apparatus.

The following description will explain the present invention concretely with reference to the drawings for illustrating an embodiment thereof FIG. 1 is a schematic perspective view for illustrating the main structure of an X-ray detection apparatus. An X-ray detection apparatus is an apparatus for making an X-ray fluorescence analysis including steps of: detecting fluorescent X-rays generated by irradiating a sample with X-rays; and measuring a fluorescent X-ray spectrum or analyzing elements contained in the sample. An X-ray detection apparatus is equipped with a sample support unit 1 for supporting a sample. The sample support unit 1 has a horizontal plate shape and supports a sample as the sample is placed thereon. The sample support unit 1 is provided with a through hole 11. A sample, which is not illustrated in FIG. 1, is placed to close the through hole 11. Actually, the main part illustrated in FIG. 1 is held in a case, which is not illustrated in the figures, together with other parts, which are not illustrated in the figures, such as a power supply unit.

Figure 2:
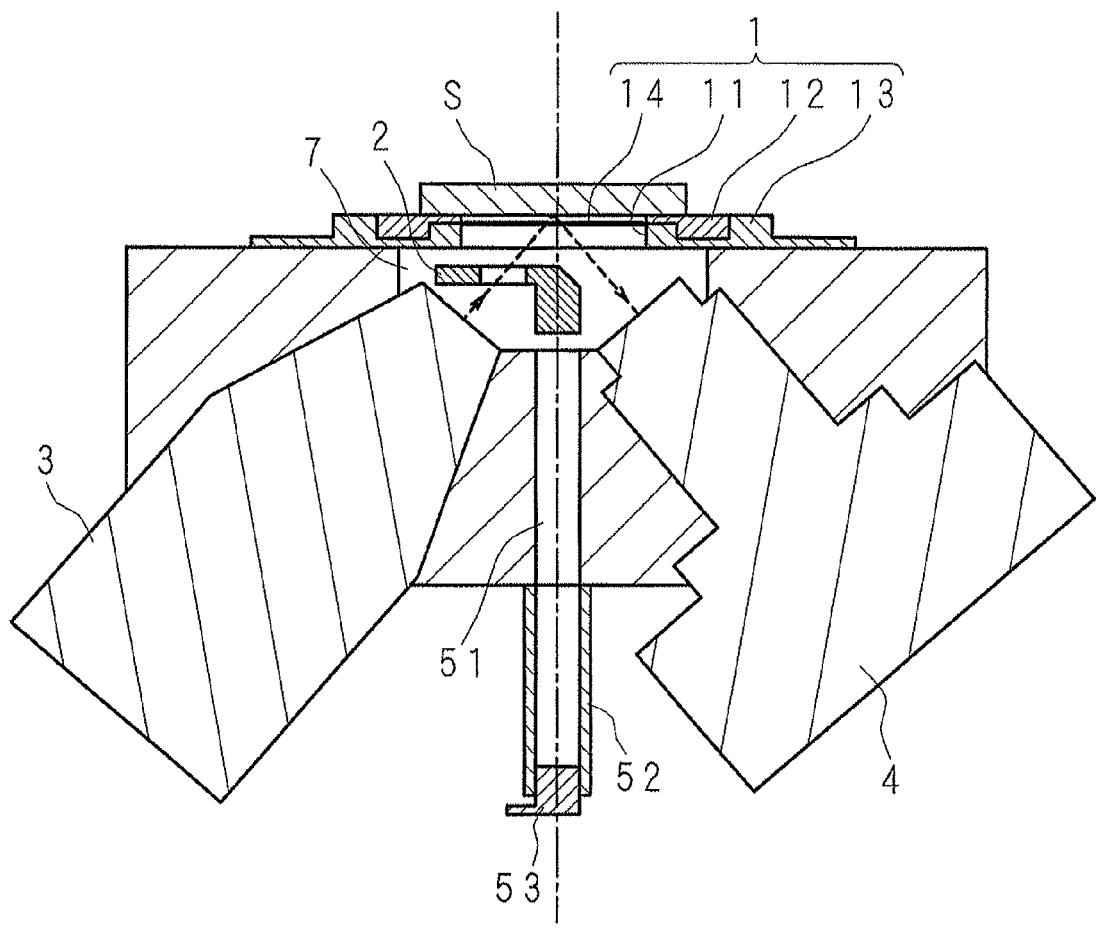
FIG. 2 is a schematic sectional view for illustrating the II-II cross section of FIG. 1.

FIG. 2 is a schematic sectional view for illustrating the II-II cross section of FIG. 1. A sample S is placed at a position to close the through hole 11 of the sample support unit 1. An X-ray irradiation unit 3 for irradiating the placed sample S with X-rays, a collimator 2 for narrowing X-rays from the X-ray irradiation unit 3, and an X-ray detector 4 for detecting fluorescent X-rays generated from the sample S are located below the sample support unit 1. Although the X-ray irradiation unit 3 and the X-ray detector 4 are illustrated in FIG. 2 as cross sections simplistically, the X-ray irradiation unit 3 and the X-ray detector 4 are actually composed of a plurality of components and also include cavities therein.

The sample support unit 1 has a base unit 13 and a detachable unit 12 which can be attached to and detached from the base unit 13. The through hole 11 is formed both at the base unit 13 and the detachable unit 12, and the base unit 13 and the detachable unit 12 form a substantially plate shape. An X-ray transparent film 14 is spread to close the through hole 11, and the X-ray transparent film 14 is fixed between the base unit 13 and the detachable unit 12. The X-ray transparent film 14 is fixed by steps of: spreading the X-ray transparent film 14 at the through hole 11 of the base unit 13 with the detachable unit 12 detached; and attaching the detachable unit 12 to the base unit 13. The through hole 11 and the X-ray transparent film 14 correspond to an X-ray transmissive window. The sample S is placed above the X-ray transparent film 14.

The X-ray irradiation unit 3 is located at a position to irradiate an undersurface of the sample S, which is placed on the sample support unit 1, with X-rays from obliquely below. The X-ray irradiation unit 3 is constituted of an X-ray tube and is located with an exit end of X-rays faced to the through hole 11 of the sample support unit 1. The X-ray detector 4 is located at a position to detect fluorescent X-rays radiated from the undersurface of the sample S, which is placed on the sample support unit 1, obliquely downward. The X-ray detector 4 is constituted of an X-ray detection element such as a silicon device and is located with an entrance end of fluorescent X-rays faced to the through hole 11 of the sample support unit 1. Moreover, the X-ray irradiation unit 3 and the X-ray detector 4 are located at symmetrical positions with respect to a hypothetical central axis, which is perpendicular to the sample support unit 1 and passes through the center of the through hole 11, and are located as proximally as practicable to the sample support unit 1. In FIG. 2, the hypothetical central axis is drawn with an alternate long and short dash line. The sample S is irradiated with X-rays from the X-ray irradiation unit 3, fluorescent X-rays are generated at the sample S, and the fluorescent X-rays are detected by the X-ray detector 4. In FIG. 2, X-rays from the X-ray irradiation unit 3 to be used for irradiation of the sample S and fluorescent X-rays, which are generated at the sample S and detected by the X-ray detector 4, are drawn with dashed lines.

Figure 3:
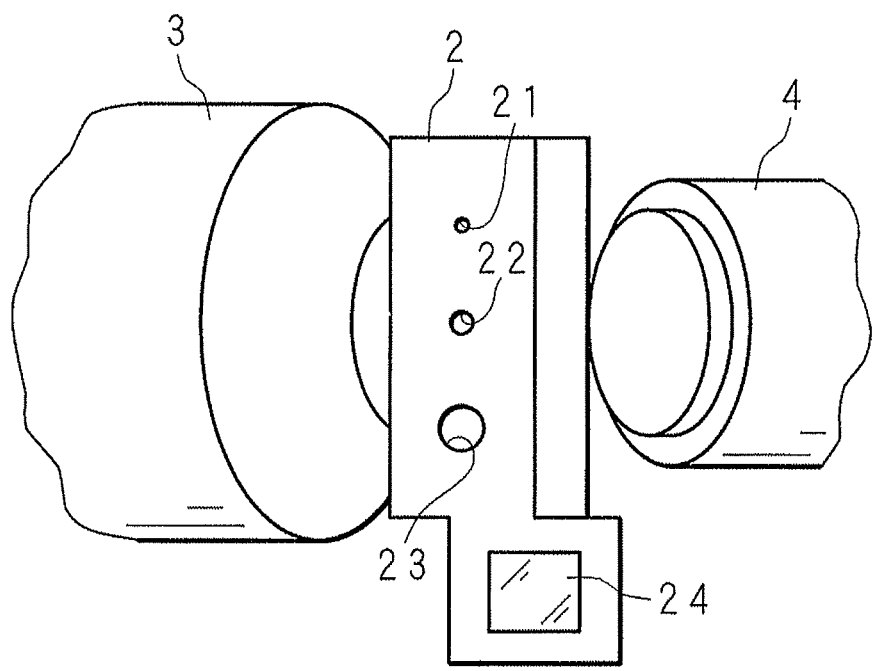
FIG. 3 is a schematic top plan view of a collimator.
Figure 4:
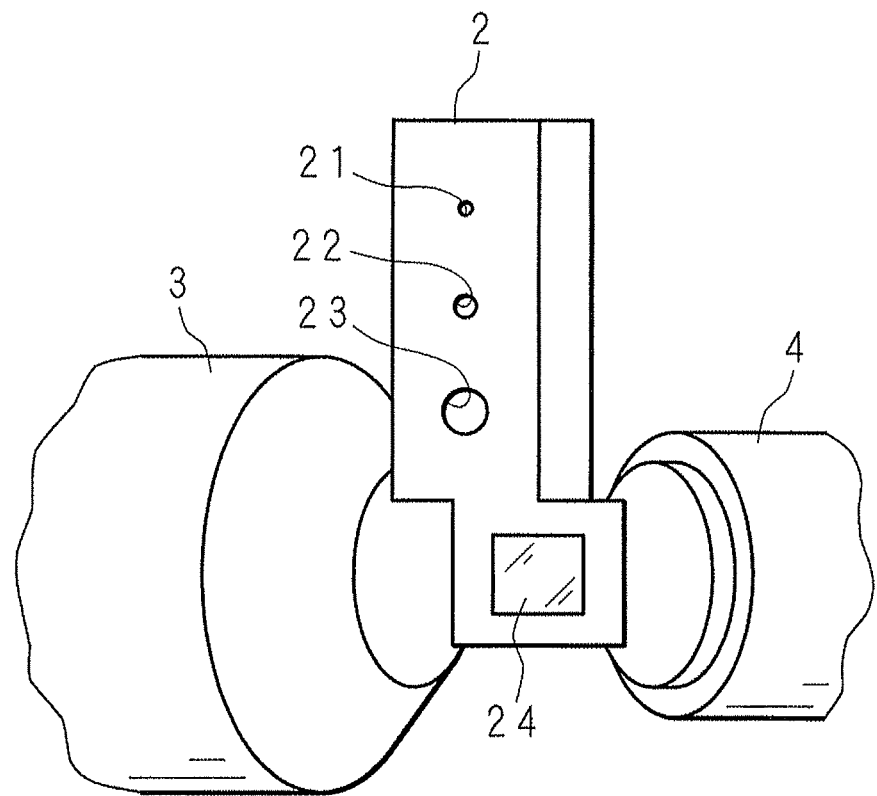
FIG. 4 is a schematic top plan view of a collimator.

The collimator 2 is located immediately below the sample support unit 1 and in an X-ray path from the X-ray irradiation unit 3 to the sample support unit 1. FIGS. 3 and 4 are schematic top plan views of the collimator 2. Actually, the sample support unit 1 is located further above the collimator 2. The collimator 2 is formed of a member to block X-rays, and a plurality of apertures 21, 22 and 23 having different diameters are formed at the collimator 2. The diameters of the apertures 21, 22 and 23 are, for example, 1.2 mm, 3 mm and 7 mm respectively. It is to be noted that the number of apertures is not limited to three but may be two or may be four or more. Moreover, there is no need to make all apertures have different diameters but it is only preferable to make at least one aperture have a diameter different from others. The apertures 21, 22 and 23 are aligned in a direction crossing a direction, in which the X-ray irradiation unit 3 and the X-ray detector 4 are aligned, in a horizontal plane.

The collimator 2 can move in a direction, in which the apertures 21, 22 and 23 are aligned, along the undersurface of the sample support unit 1. The direction of movement corresponds to a direction perpendicular to the plane illustrated in FIG. 2 and corresponds to the longitudinal direction of FIGS. 3 and 4. As the collimator 2 moves, the apertures 21, 22 and 23 are shifted and any one of the apertures 21, 22 and 23 can be positioned in the X-ray path. When any one of the apertures 21, 22 and 23 is positioned in the X-ray path, X-rays pass through the one of the apertures 21, 22 and 23 and the sample S is irradiated with the X-rays from the X-ray irradiation unit 3. Illustrated in FIGS. 2 and 3 is a state where the aperture 22 is positioned in the X-ray path. As the collimator 2 moves, an aperture through which X-rays pass is changed and the diameter of an aperture through which X-rays pass changes. As the diameter of an aperture changes, the size of X-rays to be used for irradiation of the sample S changes and the size of an analysis object part of the sample S changes. It is possible to select the size of an analysis object part of the sample S according to the objective, by selecting any one of the apertures 21, 22 and 23. The apertures 21, 22 and 23, which are located in the X-ray path from the X-ray irradiation unit 3, are positioned away from the hypothetical central axis passing through the center of the through hole 11.

The collimator 2 further has a window unit 24 which allows light to pass therethrough. The window unit 24 is constituted of a transparent member such as an acrylic plate. The window unit 24 is provided at a position along a direction in which the apertures 21, 22 and 23 are aligned. The collimator 2 can move to position the window unit 24 immediately below the through hole 11. Illustrated in FIG. 4 is a state where the window unit 24 is positioned immediately below the through hole 11. In such a state, the window unit 24 is positioned on the hypothetical central axis passing through the center of the through hole 11.

Figure 5:
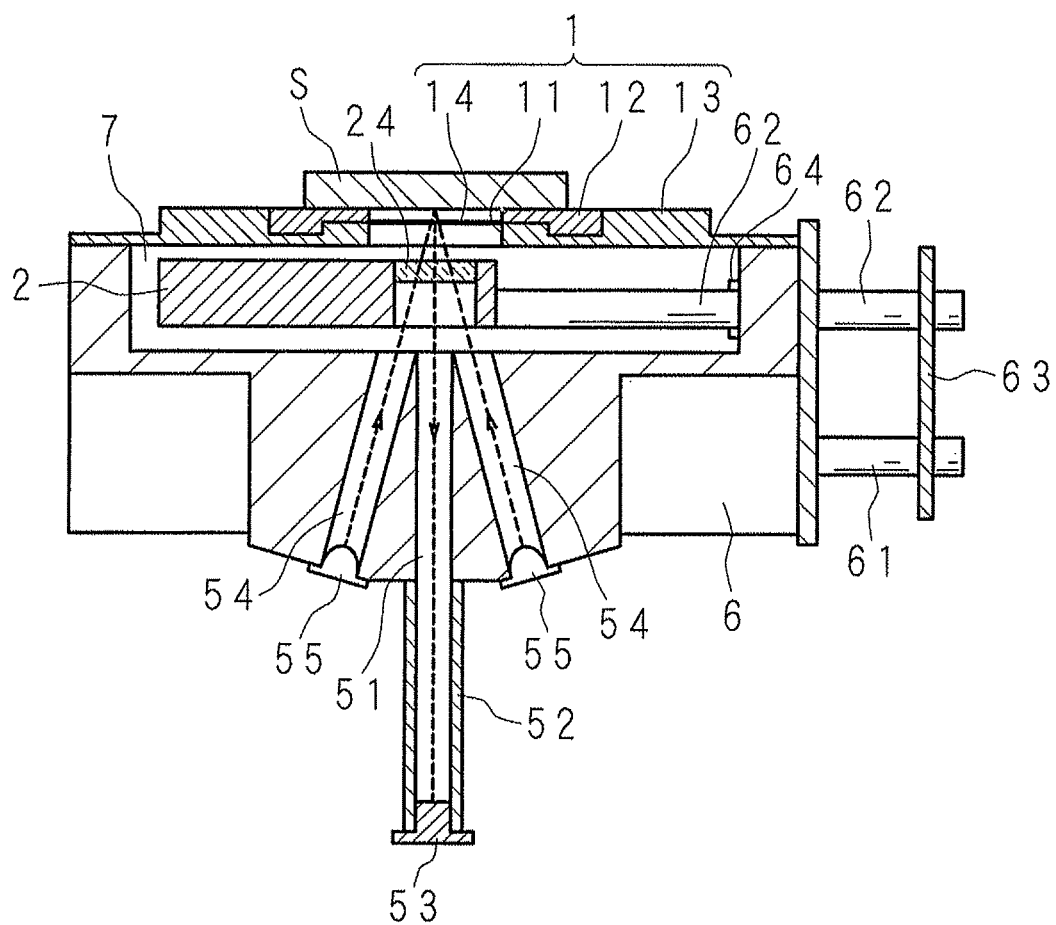
FIG. 5 is a schematic sectional view for illustrating the V-V cross section of FIG. 1.

FIG. 5 is a schematic sectional view for illustrating the V-V cross section of FIG. 1. The plane illustrated in FIG. 5 corresponds to a plane perpendicular to the plane illustrated in FIG. 2. A light guide hole 51 which allows light to pass therethrough is provided below the collimator 2. The light guide hole 51 is a hole provided in a vertical direction immediately below the through hole 11. A light guide tube 52 is connected with the lower end of the light guide hole 51, and an image sensor 53 such as a CCD (Charge Coupled Device) image censor or a CMOS (Complementary Metal Oxide Semiconductor) image sensor is equipped at the lower end of the light guide tube 52. The image sensor 53 corresponds to an imaging unit. Light guide holes 54 and 54 are provided in an oblique direction at sides of the light guide hole 51. Light emitting devices 55 and 55 such as Light Emitting Diodes are equipped at the lower end of the light guide holes 54 and 54.

Illustrated in FIG. 5 is a state where the window unit 24 is positioned immediately below the through hole 11. In such a state, light from the light emitting devices 55 and 55 passes through the light guide holes 54 and 54 and the window unit 24, and the undersurface of the sample S is irradiated with the light. Light reflected at the undersurface of the sample S passes through the window unit 24, the light guide hole 51 and the light guide tube 52, and enters the image sensor 53. In such a manner, the sample S is photographed. The size of the window unit 24 is a size to allow light to be used for obtainment of an optical image of the sample S with the image sensor 53 to pass therethrough. That is, the size of the window unit 24 is a size to ensure a visual field to photograph the sample S placed above the through hole 11 with the image sensor 53. The size of the window unit 24 is preferably larger than the size of the apertures 21, 22 and 23. In FIG. 5, light paths are drawn with dashed lines. Light from the sample S to the image sensor 53 passes through a light path substantially overlapping the hypothetical central axis passing through the center of the through hole 11. It is to be noted that an optical system, which is not illustrated in the figures, such as a lens is provided in the light guide hole 51 and the light guide holes 54 and 54, and a cover, which is not illustrated in the figures, made of a translucent material such as acrylic is provided at the upper end of the light guide hole 51 and the light guide holes 54 and 54.

The X-ray detection apparatus is equipped with a linear drive motor 6 functioning as a movement mechanism of the collimator 2. The linear drive motor 6 is located at a position lower than the sample support unit 1. The linear drive motor 6 is equipped with a drive shaft 61 and operates to drive the drive shaft 61 linearly in the longitudinal direction. The drive shaft 61 is connected with a parallel shaft 62 via a connecting plate 63. As the linear drive motor 6 drives the drive shaft 61, the parallel shaft 62 reciprocates in the longitudinal direction parallel to the drive shaft 61 in conjunction with the drive shaft 61. The parallel shaft 62 reciprocates in the lateral direction of FIG. 5. The parallel shaft 62 is connected with the collimator 2. As the parallel shaft 62 reciprocates, the collimator 2 moves along an undersurface of the sample support unit 1. Moreover, a lower side of the sample support unit 1 forms a sealed box 7. The collimator 2, an end part of the X-ray irradiation unit 3 from which X-rays exit and an end part of the X-ray detector 4 through which fluorescent X-rays enter are located in the sealed box 7. The parallel shaft 62 is piercing through a wall of the sealed box 7, and a shaft seal 64 such as an O-ring for maintaining the sealing condition is provided at the parallel shaft 62. It is possible to reduce the pressure in the sealed box 7 using a vacuum pump, which is not illustrated in the figures, or to substitute air in the sealed box 7 with another gas. Detection of fluorescent X-rays is performed preferably in a state where the pressure in the sealed box 7 is reduced.

The X-ray detection apparatus is equipped with a control unit, which is not illustrated in the figures, for controlling the operations of the linear drive motor 6. The control unit controls the operations of the linear drive motor 6 so as to control the position of the collimator 2. The control unit controls the position of the collimator 2 to locate the collimator 2 at one of a plurality of preset positions as needed. The plurality of positions for control include: positions to locate the apertures 21, 22 and 23 respectively in the X-ray path from the X-ray irradiation unit 3; and a position to locate the window unit 24 immediately below the through hole 11. By controlling the operations of the linear drive motor 6 in such a manner, it becomes possible to change the diameter of an aperture of the collimator 2 and move the window unit 24 to a position to enable photographing. The X-ray detection apparatus is also equipped with a signal processing unit, which is not illustrated in the figures, for executing signal processing for X-ray fluorescence measurement. The X-ray detector 4 outputs a signal proportional to the energy of detected fluorescent X-rays to the signal processing unit. The signal processing unit executes processing to count signals of each value and obtain the relation between energy of fluorescent X-rays detected by the X-ray detector 4 and the number of counts, that is, a fluorescent X-ray spectrum. It is to be noted that the X-ray detector 4 may be constructed to detect fluorescent X-rays separately for each wavelength. Moreover, the signal processing unit may be constructed to further execute X-ray fluorescence analysis processing of making a qualitative analysis or a quantitative analysis of elements contained in a sample on the basis of the fluorescent X-ray spectrum.

As explained above, in the X-ray detection apparatus according to the present embodiment, the movable collimator 2 is provided with the window unit 24. It is possible to photograph the sample S through the window unit 24 while the collimator 2 is at a predetermined position, although it is impossible to photograph the sample S while the collimator 2 is at a position to narrow X-rays from the X-ray irradiation unit 3. The image sensor 53 is located immediately below the through hole 11 on which the sample S is placed, so that it becomes possible to photograph the sample S without being interrupted by other components when the window unit 24 is positioned immediately below the through hole 11. Since it is possible to photograph the sample S without moving the sample S from a position where the sample S is irradiated with X-rays, it is possible to photograph the sample S at a position where the sample S is irradiated with X-rays. Accordingly, it becomes possible to photograph the sample S even in a state where the X-ray irradiation unit 3, the X-ray detector 4 and the collimator 2 are positioned proximally to each other, and therefore it becomes possible to downsize an X-ray detection apparatus which enables photographing of the sample S as well as X-ray fluorescence analysis.

Moreover, the X-ray detection apparatus realizes stable photographing, since only the collimator 2 is moved and there is no need to move an optical system to be used for photographing. Since the apertures 21, 22 and 23 and the window unit 24 of the collimator 2 are aligned in one direction and the collimator 2 moves in a reciprocating motion in the direction, it is possible to easily execute both of change of the diameter of an aperture and movement of the window unit 24 to a position to enable photographing in one action. The collimator 2 can be moved by movement of the parallel shaft 62, which is connected with the collimator 2, in the longitudinal direction by the linear drive motor 6. The movement mechanism using the linear drive motor 6 has a structure more simple than other movement mechanisms using a rack and pinion, gears or the like. A mechanism to be used for movement of the collimator 2 therefore becomes simple, which facilitates downsizing of an X-ray detection apparatus. Moreover, the movement mechanism in which the parallel shaft 62 that moves in the longitudinal direction is connected with the collimator 2 enables sealing to maintain the sealing condition only by providing the shaft seal 64 such as an O-ring at the parallel shaft 62, and therefore sealing is easier than other movement mechanisms using gears or the like. This makes it easier to maintain the sealing condition in the sealed box 7 and makes it possible to detect fluorescent X-rays in a state where the pressure in the sealed box 7 is reduced or in a state where air in the sealed box 7 is substituted with another gas. By detecting fluorescent X-rays under reduced pressure, it is possible to inhibit absorption of X-rays by air and generation of fluorescent X-rays from air, and therefore analysis of a light element contained in the sample S becomes easier.

Moreover, in the X-ray detection apparatus, all mechanisms to be used for detection of fluorescent X-rays, such as the X-ray irradiation unit 3, the X-ray detector 4 and the collimator 2, are located below the sample support unit 1, and the sample S is placed on the sample support unit 1. Since there is no structure that obstructs placement and replacement of the sample S, handling of the sample S by the user is easy and the X-ray detection apparatus offers improved convenience. The X-ray detection apparatus may control the position of the collimator 2 to position the window unit 24 immediately below the through hole 11 in a state where the X-ray irradiation unit 3 and the X-ray detector 4 are not working after detection of fluorescent X-rays has been completed. The window unit 24, which is constituted of a transparent member such as an acrylic plate, functions as a cover located immediately below the through hole 11. When the X-ray transparent film 14 tears or when the detachable unit 12 is detached to replace the X-ray transparent film 14, for example, the window unit 24 prevents falling of the sample S. The X-ray transparent film 14 tears easily especially when detection of fluorescent X-rays is completed and the sample S is replaced. By the control to position the window unit 24 immediately below the through hole 11 after detection of fluorescent X-rays is completed, it is possible to prevent falling of the sample S in a state where the X-ray transparent film 14 may tear easily. It is to be noted that the window unit 24 may be a hole not including a transparent member. In such an embodiment, it is possible to photograph the sample S, although it is impossible to prevent falling of the sample S.

It is to be noted that an X-ray detection apparatus may be constructed to narrow fluorescent X-rays generated from the sample S with a collimator, although the X-ray detection apparatus in the present embodiment is constructed to narrow X-rays from the X-ray irradiation unit 3 to be used for irradiation with the collimator 2. Moreover, an X-ray detection apparatus may be constructed to photograph a sample S with light other than visible light such as infrared light. Moreover, although a method for obtaining an optical image of a sample S in the present embodiment is to photograph the sample S, an X-ray detection apparatus may be constructed to obtain an optical image of a sample S by another method. For example, an X-ray detection apparatus may be constructed to enable observation of a sample S by executing processes of: converting an optical image of the sample S into an electric signal with the image sensor 53; generating an image of the sample S on the basis of the electric signal outputted from the image sensor 53; and displaying an image of the sample S at an internal or external display.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. An X-ray detection apparatus comprising:
an X-ray irradiation unit;
a sample support unit structured to support a sample to be irradiated with X-rays from the X-ray irradiation unit;
an X-ray detector structured to detect X-rays generated from the sample;
an imaging unit structured to obtain an optical image of the sample supported by the sample support unit by receiving light which is reflected from the sample and is not coaxial with X-rays; and
a collimator which includes a plurality of apertures having different sizes and a window unit that light used for obtaining an optical image of the sample can pass through,
wherein the collimator moves to change an aperture that X-rays pass through and moves to shift the window unit to a position that allows the imaging unit to obtain an optical image of the sample through the window unit.

2. The X-ray detection apparatus according to claim 1, wherein the plurality of apertures and the window unit of the collimator are aligned in one direction, and
the collimator can move in said one direction.

3. The X-ray detection apparatus according to claim 2, further comprising:
a shaft parallel to the one direction; and a linear drive motor, which has a drive shaft parallel to said shaft, structured to drive the drive shaft linearly in a longitudinal direction, wherein the shaft is connected with the drive shaft, and the collimator is connected with the shaft.

4. The X-ray detection apparatus according to claim 3, further comprising:

a sealed box in which an end part of the X-ray irradiation unit that X-rays exit from, an end part of the X-ray detector that X-rays enter through and the collimator are located, wherein the shaft is piercing through a wall of the sealed box and is provided with a shaft seal structured to maintain a sealing condition.

5. The X-ray detection apparatus according to claim 1, wherein the sample support unit has a horizontal plate shape and has an X-ray transmissive window on which a sample is to be placed, the imaging unit is located immediately below the sample support unit, the collimator moves along an undersurface of the sample support unit, the X-ray irradiation unit is located at a position to irradiate the X-ray transmissive window with X-rays from obliquely below, and the X-ray detector is located at a position to detect X-rays which have been transmitted by the X-ray transmissive window obliquely downward.

6. The X-ray detection apparatus according to claim 5, wherein the window unit comprises a transparent plate.

7. An X-ray detection apparatus comprising:

an X-ray irradiation unit;

a sample support unit structured to support a sample to be irradiated with X-rays from the X-ray irradiation unit;

an X-ray detector structured to detect X-rays generated from the sample;

an imaging unit structured to obtain an optical image of the sample supported by the sample support unit;

a collimator which includes a plurality of apertures having different sizes and a window unit that light used for obtaining an optical image of the sample can pass through;

wherein the collimator moves to change an aperture that X-rays pass through and moves to shift the window unit to a position that allows the imaging unit to obtain an optical image of the sample through the window unit, wherein the plurality of apertures and the window unit of the collimator are aligned in one direction, the collimator can move in said one direction, a shaft parallel to the one direction; and a linear drive motor, which has a drive shaft parallel to said shaft, structured to drive the drive shaft linearly in a longitudinal direction, wherein the shaft is connected with the drive shaft, and the collimator is connected with the shaft.

8. An X-ray detection apparatus comprising:

an X-ray irradiation unit;

a sample support unit structured to support a sample to be irradiated with X-rays from the X-ray irradiation unit;

an X-ray detector structured to detect X-rays generated from the sample;

an imaging unit structured to obtain an optical image of the sample supported by the sample support unit; and a collimator which includes a plurality of apertures having different sizes and a window unit that light used for obtaining an optical image of the sample can pass through, wherein the collimator moves to change an aperture that X-rays pass through and moves to shift the window unit to a position that allows the imaging unit to obtain an optical image of the sample through the window unit, the sample support unit has a horizontal plate shape and has an X-ray transmissive window on which a sample is to be placed, the imaging unit is located immediately below the sample support unit, the collimator moves along an undersurface of the sample support unit, the X-ray irradiation unit is located at a position to irradiate the X-ray transmissive window with X-rays from obliquely below, and the X-ray detector is located at a position to detect X-rays which have been transmitted by the X-ray transmissive window obliquely downward.

\* \* \* \* \*